United States Patent [19]

Lafon

[11] Patent Number: 4,835,315
[45] Date of Patent: May 30, 1989

[54] FLUOROPHENACYL-AMINE DERIVATIVES AND APPLICATION THEREOF IN THERAPEUTICS

[75] Inventor: Louis Lafon, Paris, France
[73] Assignee: Laboratoire L. Lafon, France
[21] Appl. No.: 68,702
[22] Filed: Jul. 1, 1987

Related U.S. Application Data

[63] Continuation of Ser. No. 867,409, May 14, 1986, abandoned, which is a continuation of Ser. No. 716,337, Mar. 26, 1985, abandoned, which is a continuation-in-part of Ser. No. 443,934, Nov. 23, 1982, abandoned, which is a continuation of Ser. No. 252,506, Apr. 8, 1981, abandoned.

[51] Int. Cl.$^4$ ..................... A61K 31/135; C07C 91/16
[52] U.S. Cl. .................................. 564/363; 514/653; 564/345; 260/501.17
[58] Field of Search ................... 564/363, 364, 545; 514/554, 655

[56] References Cited

U.S. PATENT DOCUMENTS

| | | | |
|---|---|---|---|
| 3,225,096 | 12/1965 | Mills et al. | 564/345 X |
| 3,344,188 | 9/1967 | Wollweber et al. | 564/363 |
| 4,372,969 | 2/1983 | Lafon | 564/363 X |

FOREIGN PATENT DOCUMENTS 1043519  9/1966  United Kingdom ................ 564/363

OTHER PUBLICATIONS

Lands, "Journal Pharmacal. Exptl. Therap.", vol. 106, pp. 440-443 (1952).
Levy et al., "Journal Pharmacal. Exptl. Therap.", vol. 133, pp. 202-210 (1961).
Koshimako et al., "Chemical Abstracts", vol. 50, p. 90, Section 132710z (1979).
Hideo et al., "Chemical Abstracts", vol. 92, p. 652, Section No. 198089b (1980).
Paspribu et al., "Chemical Abstracts", vol. 82, p. 12, Section 106173s (1945).
Hideo et al., "Chemical Abstracts", vol. 78, p. 345, Section 147538a (1973).

Primary Examiner—Robert V. Hines
Attorney, Agent, or Firm—Eric P. Schellin; Jerome J. Norris

[57] ABSTRACT

The present invention relates to new compounds belonging to the family of fluorophenacyl-amine derivates of formula:

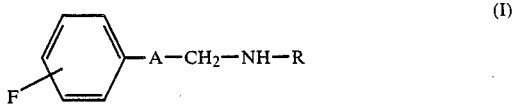

[wherein A is CO or CHOH and R is CH(CH$_3$)$_2$ or C(CH$_3$)$_3$] and selected from the group consisting of N-(4-fluorophenacyl)-isopropylamine, N-(2-fluorophenacyl)-tertiarybutylamine, 1-(2-fluorophenyl)-2-tertiarybutylamino-1-ethanol, 1-(4-fluorophenyl)-2-tertiarybutylamino-1-ethanol, and their addition salts, These new derivatives are useful in therapeutics, particularly as anti-aggressive agents, anti-anorexia nervosa agents, sedative agents, and CNS- antidepressants.

3 Claims, No Drawings

FLUOROPHENACYL-AMINE DERIVATIVES AND APPLICATION THEREOF IN THERAPEUTICS

This application is a continuation of Ser. No. 06/867,409, filed 05/14/86, which is a continuation of Ser. No. 06/716,337, filed 03/26/85, which is a continuation-in-part of Ser. No. 06/443,934, filed 11/23/82 and which is a continuation of Ser. No. 06/252,506, filed 04/08/81, all of which are abandoned.

BACKGROUND

The present invention relates, by way of new industrial products, to fluorophenacyl-amine derivatives, and also to the application thereof in therapeutics as unexpectedly and significantly superior anti-anorexia nervosa agents and anti-aggressive agents as well as beta-stimulating agents and antidepressant agents In the following specification, fluorophenacylamine derivates are understood to mean not only compounds having a fluorophenacyl group or formula $F-C_6H_4-CO\ CH_2-$, but also a $\beta$-hydroxyfluorophenethyl group of formula $F-C_6H_4-CHOH-CH_2-$, which derives from the preceding one by reduction of the carbonyl function into alcohol function.

Compounds of the 2-amino-1-(halogenophenyl)-1-ethanol type are included in the formula of French Pat. No. 1 503 517 and presented as antidiuretic agents. However, it should be noted that this French patent describes no 1-(fluorophenyl), 1-(chlorophenyl), 1-(bromophenyl) and 1-(iodophenyl) derivatives, nor does it suggest their potential actions on the CNS.

It is known that fluorophenacyl-amine derivatives belonging to the family of 2-amino-1-(fluorophenyl)-1-ethanols have already been described. In particular, the article by A.M. Lands, J. Pharmacol. Exptl. Therap. 106, 440–443 (1952) disclosed 1-(3-flurophenyl)-2-isopropylamino-1-ethanol and 1-(3-fluorophenyl)-2-tertiary-amino-1-ethanol as being weak pressor agents. The article by L. Villa, et al., Il Farmaco Ed. Scientifica, 24 (No. 3), 329–340 (1969), discloses 1-(4-fluorophenyl)-2-isopropylamino-1-ethanol and 1-(2-fluorophenyl)-2-isopropylamino-1-ethanol. These known fluorinated products act on the CNS but they have no, or only slight, aggression-reducing effect. Further, analogous compounds are also disclosed as being adrenergic blocking agents in the article by B. Levy, et al., J. Phamarmacol. Exptl. Therap., 133, 202-210 (1961); as appetite-supressing agents in U.S. Pat. Nos. 3,313,687 (Siemer) and 3,465,039 (Seimer); as CNS-stimulant and antidepressant agents in U.S. Pat. No. 3,819,706 (Mehtay; and as anti-diuretic agents in British Pat. No. 1,043,510.

It has been unexpectedly found that the new fluorophenacyl-amine derivatives of the present invention, which act on the CNS, have particularly advantageous antiaggressive and anti-anorexia nervosa properties from the therapeutical standpoint.

According to the invention, a compound belonging to the family of fluorophenzcyl-amine derivatives of formula:

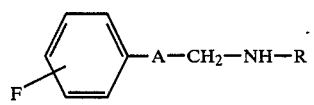

(I)

wherein A is CO or CHOH, and R is CH(CH$_3$)$_2$ or C(CH$_3$)$_3$, is recommended as new industrial product, particularly useful in therapeutics, said compound being characterised in that it is selected from the group consisting of N-(4-fluorophenacyl)-isopropylamine, N-(2-fluorophenacyl)-tertiobutylamine, 1-(2-fluorophenyl)-2-tertiarybutylamino-1-ethanol, 1-(4-fluorophenyl)-2-tertiaryamino-1-ethanol, and their addition salts.

From these products, the preferred compounds from the therapeutical standpoint are N-(4-flurophenacyl)-isopropylamine and its salts, particularly the hydrochloride.

Addition salts are understood here to mean the acid addition salts obtained by reacting a free base of formula I with an inorganic or organic acid, and the ammonium slats. Among the acids which may be used for salifying the bases of formula I, the following may be particularly mentioned: hydrochloric, hydrobromic, nitric, sulphuric, acetic, propionic, oxalic, fumaric, maleic, succinic, benezoic, cinnamic, mandelic, citric, malic, lactic, tartaric, p-toluenesulphonic and methanesulphonic acids. Among the compounds enabling ammonium salts to be obtained, particular mention may be made of ICH$_3$ and ClCH$_3$. The acid addition salts are the preferred salts, and, among the latter, the most advantageous are the hydrochlorides.

The fluorophenacyl-amine derivatives of this invention may be prepared according to a method known per se, by application of conventional reactional mechanisms. The recommended process for preparation consists of the following:

(1) in obtaining a "carbonyl" compound (A=CO) by reacting a fluorophenacyl halide of formula

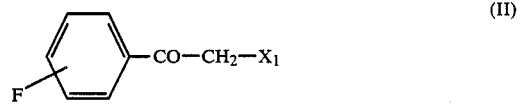

(II)

(wherein X$_1$ is Cl or Br) with an amine of formula $$H_2NR \qquad \qquad (III)$$

(wherein R is defined as hereinabove), under reflux for at least 1 hour in an alcohol, preferably methanol, then (2) if necessary, in obtaining an "alcohol" compound (A=CHOH) by reducing the corresponding carbonyl derivative, in particular with NaBH$_4$.

The compounds according to the invention are all active on the CNS and also have interesting cardiovascular effects. In particular, they act on the CNS as sedative agents, antidepressants and superior antiaggressive agents and are unexpectedly indicated in the treatment of anorexia nervosa as well as depression.

DETAILED DESCRIPTION

According to the invention, a therapeutic composition is recommended, particularly useful in the treatment of aggression, anorexia nervosa and depression, characterized in that it contains, in association with a physiogically acceptable excipient, at least one fluorophenacyl-amine derivative according to the present invention or one of its nontoxic addition salts, the active ingredient being, of course, administered at a pharmaceutically effective amount.

Comparative tests have been carried out to demonstrate those effects on animals which distinguish the products according to the present invention from their closest known fluorinated analogues. Among these tests, those concerning the antiaggressive properties and anti-anorexia nervosa properties have been summarized. More particularly, the reduction of the intergroup aggressiveness was assessed according to the following technique: after 3 week's residence on either side of an opaque partition separating their cage at the center, groups of 3 male mice each weighing about 20g receive by interperitoneal route the products to be tested, in solution in distilled water, the control animals receiving only distilled water by I. P. route. Half an hour later, the two groups of the same cage are brought together by withdrawing the partition and the number of fights which take place in 10 minutes is noted. 3 cages are used for each product to be tested and 6 cages for the control batch not receiving the products to be tested.

The results of Table I hereinafter give the reduction in intergroup aggressiveness with respect to the control batch, all the products to be tested being administered at the dose of 8 mg/kg by I.P. route. These results show (i) that the product according to the invention (Examples 1 to 5) have a clearly greater antiaggressive effect than that of their known analogues (CPI to CP4) and (ii) that there is no structure-activity relationship.

from the closest prior art compounds. These tests were concerned with the determination of weight variation after treatment in animal and in female human patients suffering from anorexia nervosa.

The first series of experiments assessed the weight variation of adult female rats (weighing approximately 190 g each) receiving a daily dose of from 3 to 10 mg/kg of the compound to be tested (batch of 10 animals per product) with respect to control animals (batch of 15 animals). After three weeks of treatment with the compounds hereinafter listed in Table II, the results are summarized in Table III and are expressed as weight variation percentages. In these tables the compounds of the present invention are referenced as Ex 1–Ex 5, and the comparative compounds of the prior art are referenced CP 1–CP 14.

It was expected that all tested compounds should exhibit an appetite depressing action expressed as a negative weight variation after treatment. The results show that surprisingly Ex 3 (CRL 40827) and Ex 5 (CRL 40854) as well as CP 1-2 and CP 4 cannot be considered as appetite supressing substances. Unlike the other compounds which reduce the animal weight by more than 10%, these compounds resulted in a positive weight variation.

TABLE I

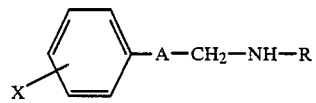

| Product | Code No. | X | A | R | Dose mg/kg | reduction of intergroup aggressiveness |
|---|---|---|---|---|---|---|
| Example 1 (a) | CRL 40727 | 4-F | CO | CH(CH$_3$)$_2$ | 8 | 75% |
| Example 2 (a) | CRL 40828 | 2-F | CO | C(CH$_3$)$_3$ | 8 | 61% |
| Example 3 (a) | CRL 40827 | 2-F | CHOH | C(CH$_3$)$_3$ | 8 | 76% |
| Example 4 (b) | CRL 40827A | 2-F | CHOH | C(CH$_3$)$_3$ | 8 | 78% |
| Example 5 (a) | CRL 40854 | 4-F | CHOH | C(CH$_3$)$_3$ | 8 | 69% |
| CP1 (a) (c) | — | 3-F | CHOH | CH(CH$_3$)$_2$ | 8 | 5% |
| CP2 (a) (c) | — | 3-F | CHOH | C(CH$_3$)$_3$ | 8 | 31% |
| CP3 (a) (d) | CRL 40853 | 4-F | CHOH | CH(CH$_3$)$_2$ | 8 | 40% |
| CP4 (a) (d) | — | 2-F | CHOH | CH(CH$_3$)$_2$ | 8 | 6% |

Notes
(a): hydrochloride;
(b): fumarate;
(c): described by A. M. LANDS;
(d): described by L. VILLA et al It was surprisingly discovered that compounds according to the present invention exhibit an unexpected and valuable action against anorexia nervosa. It was generally thought in the prior art that CNS-active substances which exhibit beta-stimulant and antidepressant properties would also exhibit an anorexigenic or appetite-supressant effect. See, for example, U.S. Pat. Nos. 3,313,687 (Siemer), 3,465,039 (Siemer), and 3,819,706 (Mehta). However, a recently published clinical assay by F. Lang, et al. appearing in Societe Medico-Psychologique-Meeting of Monday July 4, 1983, shows that the compound of Example 3 of the present invention (Code No. CRL 408227) is a beta-stimulant and antidepressant agent which exhibits an unexpected action against anorexia nervosa. Accordingly, comparative tests were carried out to demonstrate this effect and to distinguish the compounds of to the present invention weight variation.

TABLE II

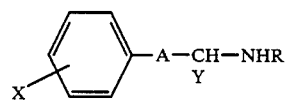

| Product | Code number | X | Y | A | R |
|---|---|---|---|---|---|
| Ex 1 (a) | CRL 40 727 | 4-F | H | CO | CH(CH$_3$)$_2$ |
| Ex 2 (a) | CRL 40 828 | 2-F | H | CO | C(CH$_3$)$_3$ |
| Ex 3 (a) | CRL 40 827 | 2-F | H | CHOH | C(CH$_3$)$_3$ |
| Ex 4 (b) | CRL 40 827A | 2-F | H | CHOH | C(CH$_3$)$_3$ |
| Ex 5 (a) | CRL 40 854 | 4-F | H | CHOH | C(CH$_3$)$_3$ |
| CP 1 (a) (c) | — | 3-F | H | CHOH | CH(CH$_3$)$_2$ |
| CP 2 (a) (c) | — | 3-F | H | CHOH | C(CH$_3$)$_3$ |

TABLE II-continued

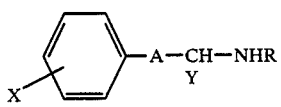

| Product | Code number | X | Y | A | R |
|---|---|---|---|---|---|
| CP 3 (a) (d) | CRL 40 853 | 4-F | H | CHOH | CH(CH₃)₂ |
| CP 4 (a) (d) | — | 2-F | H | CHOH | CH(CH₃)₂ |
| CP 5 (a) (e) | — | 3-F | CH₃ | CO | C(CH₃)₃ |
| CP 6 (a) (f) | — | 3-F | CH₃ | CO | CH(CH₃)₂ |
| CP 7 (a) (g) | — | 3-F | CH₃ | CHOH | C(CH₃)₃ |
| CP 8 (a) (h) | — | 3-F | CH₃ | CHOH | CH(CH₃)₂ |
| CP 9 (a) (f) | — | 3-F | H | CO | C(CH₃)₃ |
| CP 10 (a) (i) | — | 4-Cl | CH₃ | CO | CH₂CH₃ |
| CP 11 (a) (j) | — | H | H | CHOH | C(CH₃)₃ |
| CP 12 (a) (j) | — | 3-OH | H | CHOH | CH(CH₃)₂ |
| CP 13 (a) (k) | — | 2-Cl | H | CHOH | C(CH₃)₃ |
| CP 14 (a) (k) | — | 4-Cl | H | CHOH | C(CH₃)₃ |

Notes:
(a): hydrochloride;
(b): fumarate;
(c): disclosed by A. M. LANDS;
(d): disclosed by L. VILLA et al., Il Farmaco Ed. Scientifica, 24 (No. 3), 329-340 (1969)
(e): disclosed by MEHTA
(f): isomer of Ex 2 suggested by MEHTA
(g): disclosed as intermediate product in published Danish pat. appl. No. 134 984;
(h): isomer of Ex 3 suggested by MEHTA
(i): disclosed by SIEMER
(j): laevoisomer disclosed in Brit. patent No. 1,043,510(*) suggested by WOLLWEBER
(*) and in U.S. Pat. No. 3,344,188 (WOLLWEBER)

TABLE III
WEIGHT VARIATION OF ADULT FEMALE RATS

| Product | Code No | dose | weight variation % (a) |
|---|---|---|---|
| Ex 1 | CRL 40 727 | 10 mg/kg | −10.1 (b) |
| Ex 2 | CRL 40 828 | 5 mg/kg | −12.2 (b) |
| Ex 3 | CRL 40 827 | 5 mg/kg | +0.2 |
| Ex 4 | CRL 40 827A | 5 mg/kg | −0.1 |
| Ex 5 | CRL 40 854 | 5 mg/kg | +0.3 |
| CP 1 | — | 5 mg/kg | −0.1 |
| CP 2 | — | 10 mg/kg | +0.3 |
| CP 3 | CRL 40 853 | 5 mg/kg | −10.5 (b) |
| CO 4 | — | 5 mg/kg | −1.4 |
| CP 5 | — | 10 mg/kg | −15.3 (b) |
| CP 6 | — | 10 mg/kg | −16.4 (b) |
| CP 7 | — | 5 mg/kg | −17.3 (b) |
| CP 8 | — | 10 mg/kg | −14.2 (b) |
| CP 9 | — | 10 mg/kg | −10.3 (b) |
| CP 10 | — | 5 mg/kg | −18.1 (b) |
| CP 11 | — | 10 mg/kg | −8.5 |
| CP 12 | — | 5 mg/kg | −7.3 (b) |
| CP 13 | — | 5 mg/kg | −15.4 (b) |
| CP 14 | — | 5 mg/kg | −13.2 (b) |

Note
(a) with respect to the control animals
(b) statistically significant

In a second series of experiments women suffering from anorexia nervosa were treated with Ex 3, Ex 5, CP1, CP2 and CP4 to determine which products would induce weight uptake. Those compounds which induce the expected prior art weight reduction were not utilized in this series of tests to avoid the ethical problem that may have resulted from administering potential appetite-depressing agents to anorexia nervosa subjects. The results of this series of experiments are summarized hereinafter in Table IV. In conjunction with a normal diet, patients were given either a placebo (Treatment A), or one of the compounds to be tested (Treatments B-F) at a daily dose of 3 mg per os (more precisely, one tablet at breakfast time and one tablet at dinner time, each tablet containing 1.5 mg of compound to be tested) for 30 days. These results show that Ex 3 (which produces a weight variation of +4.3 to +14.1 kg) and Ex 5 (which produces a weight variation of +4.1 to +10 kg) confirm the results obtained by F. Lang, et al. and demonstrate the effectiveness of these products as antianorexia nervosa compounds.

TABLE IV
CLINICAL RESULTS

| Patient | age year | ideal weight kg (a) | weight before treatment kg | treatment (b) | weight variation after treatment kg |
|---|---|---|---|---|---|
| 1 | 18½ | 47 | 32.3 | A | +0.1 |
| 2 | 19 | 50 | 37.6 | A | −0.2 |
| 3 | 24 | 50 | 36 | A | −0.2 |
| 4 | 16½ | 49 | 31.5 | A | +0.1 |
| 5 | 16½ | 45 | 29.7 | A | (c) |
| 6 | 19 | 50 | 31.4 | A | +0.1 |
| 7 | 23 | 48 | 30.3 | A | −0.1 |
| 8 | 31 | 45 | 28.9* | A | +0.1 |
| 11 | 25 | 48 | 31.5 | B | +11.1 |
| 12 | 19½ | 50 | 30.6 | B | +12.6 |
| 13 | 16½ | 52 | 32 | B | +4.5 |
| 14 | 15½ | 48 | 32.6 | B | +7.2 |
| 15 | 20 | 49 | 31.5 | B | +8.1 |
| 16 | 20½ | 49 | 33.4 | B | +4.3 |
| 17 | 20 | 50 | 35 | B | +5 |
| 18 | 21 | 46 | 29.7 | B | +14.1 |
| 19 | 18 | 51 | 31 | B | +7.3 |
| 20 | 32 | 45 | 29.3 | B | +10.7 |
| 21 | 21 | 46 | 30.5 | C | +4.5 |
| 22 | 19½ | 50 | 32 | C | +7.8 |
| 23 | 17 | 52 | 35 | C | +10 |
| 24 | 28 | 46 | 29.5 | C | +4.1 |
| 25 | 18½ | 49 | 30.5 | C | +7.5 |
| 31 | 19 | 48 | 31 | D | +0.2 |
| 32 | 19½ | 48 | 33 | D | −0.2 |
| 33 | 27 | 45 | 30.8 | D | (c) |
| 34 | 18 | 50 | 29.4 | D | (c) |
| 35 | 16½ | 48 | 30.5 | D | +0.1 |
| 41 | 24½ | 48 | 31 | E | −0.1 |
| 42 | 19 | 48 | 32.3 | E | −0.3 |
| 43 | 18½ | 49 | 29.5 | E | +0.1 |
| 44 | 29 | 45 | 31.2 | E | −0.2 |
| 45 | 21 | 50 | 32.5 | E | −0.1 |
| 51 | 22 | 45 | 31.8 | F | 0 |
| 52 | 27 | 47 | 30.5 | F | (c) |
| 53 | 21 | 45 | 29.8 | F | −0.3 |
| 54 | 19 | 45 | 32.1 | F | +0.2 |
| 55 | 17½ | 50 | 31.2 | F | −0.1 |

Notes
(a) in view of patient age and heigth
(b) nature of treatment:
A placebo for 30 days
B daily dose of 3 mg of Ex 3 for 30 days
C daily dose of 3 mg of Ex 5 for 30 days
D daily dose of 3 mg of CP 1 for 30 days
E daily dose of 3 mg of CP 2 for 30 days
F daily dose of 3 mg of CP 4 for 30 days
(c) treatment stopped since untolerated Some examples of preparation have been given hereinafter by way of non-limiting illustration.

PREPARATION I

Obtaining of the hydrochloride of N-(4-fluorophenacyl)-isopropylamine

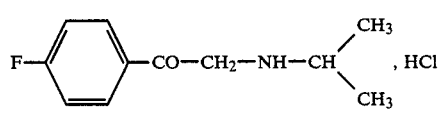

(Example 1: Code No.: CRL 40727)

25 ml of bromine are poured, dropwise, into a solution, cooled by an ice bath, of 69 g(0.5 mol) of parafluoroacetophenone in 100 ml of acetic acid. The mixture is stirred for one hour and evaporated to dryness. The residue is taken up in 100 ml of methanol and the solution thus obtained is poured in a solution of 210 ml of isopropylamine in 100 ml of methanol. It is refluxed for 2 hours, and evaporated to dryness. The residue is taken up in water, the free base of the expected product is extracted with ethyl acetate, the solvent is dried and the hydrochloride is precipitated by hydrochloric ethanol. By recrystallisation in an acetone-methanol (1:1) v/v mixture, 17.2 g (yield: 14.8%) of CRL 40727 are obtained. m.p. 207° C. (with decomposition).

Analysis: % N measured=6.01%.
% N theoretical=6.04%.

PREPARATION II

Obtaining of the hydrochloride of N-(2-fluorophenacyl)-tertiarybutylamine

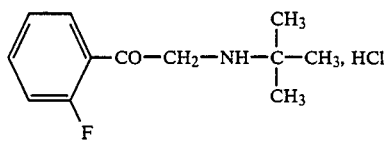

(Example 2; Code No.: CRL 40828)

50g (0.362 mol) of orthofluoroacetophenone are dissolved in 75 ml of acetic acid. The mixture is cooled by an ice bath and 18.1 ml of bromine are poured dorpwise. It is left in contact for 1 hour, evaporated to dryness and the residue is taken up in 100 ml of methanol. The solution thus obtained is poured into a solution of 132 g of tertiobutylamine in 100 ml of methanol. It is refluxed for 1 hour, evaporated to dryness, the residue is taken up in water, extracted with ether and the expected hydrochloride is precipitated by hydrochloric ethanol. By recrystallisation in an acetone-ethanol (1:1) v/v mixture, 18 g (yield=20%) of CRL 40828 are obtained. m.p.=240° C. (with decomposition).

Analysis: % N measured=5.74%.
% N theoretical=5.7%.

PREPARATION III

Obtaining of the hydrochloride of 1-(2-fluorophenyl)-2-tertiarybutylamino-1-ethanol.

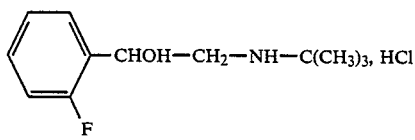

(Example 3; Code No.: CRL 40827)

0.04 mol of N-(2-fluorophenacyl)-tertiarybutylamine (free base of the CRL 40828) is dissolved in 120 ml of methanol. Cooling is effected to −5° C. and 3 g of sodium borohydride are added. It is left in contact for 1 hour. The excess NaBH4 remaining in the reactin medium is destroyed by means of 5 ml of acetic acid, then the mixture is evaporated to dryness. The residue of evaporation is taken up in water, the pH is adjusted to 11 by means of NaOH, extracted with ether, the ethereal phase is washed with water and said ethereal phase is dried over MgSO4. After filtration, the free base is collected then the expected hydrochloride is precipitated by means of hydrochloric ethanol. By recrystallization in an acetone-ethanol (1:1) v/v mixture, 8 g (yield: 80%) of CRL 40827 are obtained. m.p.=180.5° C.

Analysis: % N measured=5.60%.
% N theoretical=5.65%.

PREPARATION IV

Obtaining of the fumarate of 1-(2-fluorophenyl)-2-tertiarybutylamino-1-ethanol (Example 4; Code No. CRL 40827 A).

By reacting 1-(2-fluorophenyl)-2-tertiarybutylamine-1-ethanol (free base obtained in Preparation III) with fumaric acid, CRL 40827A is obtained. m.p. 195°-200° C. (with decomposition).

PREPARATION V

Obtaining of the Hydrochloride of 1-(4-fluorophenyl)-2-tertiarybutylamino-1-ethanol

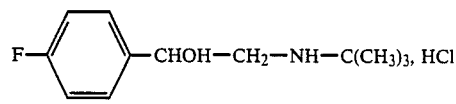

(Example 5: Code No.: CRL 40854)

50 g (0.289 mol) of α-chloro-p-fluoroacetophenone are dissolved in 900 ml of methanol. The mixture is cooled to −5° C. and 5.80 g of NaBH4 are added. It is left in contact for 1 hour then 10 ml of acetic acid are added. 151 ml of tertiarybutylamine are added and the mixture is refluxed for 12 hours. It is evaporated to dryness and the residue of evaporation is taken up in distilled water. The free base which has crystallised is filtered off and, by recrystallisation in hexane, 39 g (yield 63%) of 1-(4-fluorophenyl)-2-tertiarybutylamino-1-ethanol are obtained. m.p. 117° C.

This base is dissolved in diethyl ether, the hydrochloride is precipitated by means of hydrochloric ethanol. By filtration and drying in vacuo over P2O5, 44 g (yield: 61%) of CRL 40854 are obtained. m.p. 176° C.

CRL 40854 may also be prepared according to the process of preparation III, when replacing the N-(2-fluorophenacyl)-tertiarybutylamine by N-(4-fluorophenacyl)-tertiarybutylamine.

Additional tests carried out with the preferred products according to the present invention have been summarized hereinafter.

(A) Tests relative to CRL 40727 (Example 1)

1. Toxicity

The maximum non-lethal dose, LD-O, is greater than 128 mg/kg and less than 256 mg/kg, in the mouse, by I.P. route.

2. Action on the CNS

CRL 40727 has a certain number of sedative-type effects, namely:
sedation and hyporeactivity in the mouse,
hypomotility and reduction of aaggressiveness in the mouse,
hyopthermia and potentiation of the hypothermia-inducing effects of apomorphine, oxotremorine and reserpine,
moderate antagonism of the stereotypies induced by amphetamine.

3. Action on the cardiovascular system (a) By the intraveinous route

Two dogs receive CRL 40727 by the intraveinous route, in perfusion in 6 minutes, at the successive doses of 0.1 mg/kg, 1 mg/kg, 2.5 mg/kg/ 5 mg/kg, 10 mg/kg and 20 mg/kg. Their arterial pressure, cardiac frequency, flow rate of the femoral artery and rectal temperature are measured.

The following is observed.

CRL 40727 increases the flow rate of the femoral artery from the dose of 1 mg/kg; the effect increases with the dose, up to 10 mg/kg, dose for which +140% is attained.

From 5 mg/kg, the differential arterial pressure increases; the diastolic and average arterial pressures reduce from 10 and 20 mg/kg respectively.

The cardiac frequency is not clearly modified.

The skin becomes pink from 2.5 to 10 mg/kg.

The bilary liquid remains yellow; the rectal temperature is not modified.

Tachycardia induced by isoprenaline is reduced, the cardiac frequency passes on average to 182 beats/min after 10 mg/kg, whilst it was 215 beats/min in the control; hypotension is not modified.

A complementary experiment was undertaken; one dog receives an additional dose of 40 mg/kg I.V. of CRL 40727, and a greater hypotension is observed than at the preceding dose, the bilary liquid remaining yellow; a second dog receives a reference product, the hydrochloride of (2, 4, 6-trimethoxyphenyl)-3-pyrrolidinopropyl)-ketone—which is described in British Pat. No. 1,325,192, is coded LL 1656 and is marketed under the name FONZYLANE—at the dose of 6 mg/kg I.V. and it is observed that the rate of flow of the femoral artery does not increase more with LL1656 than with the dose of 10 mg/kg of CRL 40727.

(b) By the intraduodenal route

Three dogs receive CRL 40727 by the intraduodenal route at the successive doses of 1 mg/kg, 2.5 mg/kg, and 10 mg/kg. The same parameters as hereinabove are measured. The following is observed.

CRL 40727 clearly increases the rate of flow of the femoral artery from the dose of 2.5 to 5 mg/kg; the effect increases only slightly with the dose. From 10 mg/kg, a hypotensive action is manifested. The skin becomes very slightly pink from 2.5 mg/kg.

The biliary liquid remains yellow. The rectal temperature is not modified.

Tachycardia induced by isoprenaline is reduced. The cardiac frequency passes on average to 165 beats/min after 10 mg/kg of CRL 40727, whilst it reached 220 beats/min in the control. Hypotension is not modified.

Complementary tests were undertaken; one dog receives an additional dose of 20 mg/kg by I.D. route. A greater hypotensive action is observed, without additional vasodilator effect. The same result is obtained on another dog in which are injected 5 mg/kg I.V. of CRL 40727 at the end of the test. Moreover, the LL 1656 injected thereafter by the intraveinous route, at the dose of 6 mg/kg, does not cause additional vasodilation.

In conclusion, the results obtained by the intraveinous route and by the intraduodenal route are difficult to compare, hypotension occurring in the dogs treated by the intraveinous route only from 20 mg/kg, whilst it appears with the same intensity in the dogs treated by the intraduodenal route at 10 mg/kg.

The vasodilator action of CRL 40727 is perhaps due to a $\beta_2+$ action; no $\beta_1+$ action is observed (no tachycardia), no bradycardia; on the contrary, the tachycardia-inducing action of isoproterenol is reduced. Moreover, it will be noted that the biliary liquid remains yellow, even after the accumulated dose of 38.5 mg/kg I.V.

(B) Tests Relative to CRL 40827 (Example 3)

CRL 40827, in solution in distilled water, was administered by the intraperitoneal route in a volume of 20 ml/kg in the male mouse and a volume of 5 ml/kg in the male rat.

1. Toxicity

The maximum non-lethal dose, LD-O, is greater than 64 mg/kg and less than 128 mg/kg in the male mouse.

2. Action on the CNS

Interaction with apomorphine (a) Mouse

Batches of 6 mice receive CRL 40827 half an hour before the subcutaneous injection of apomorphine at the does of 1 or 16 mg/kg. It is observed that, at doses of 0.5 mg/kg and 2 mg/kg and especially 8 and 32 mg/kg, CRL 40727 clearly opposes the hypothermia-inducing action of the strong dose of apomorphine but does not modify the behaviour of verticalisation and the stereotypies.

(b) Rat

CRL 40827 is administered to batches of 6 rats half an hour before subcutaneous injection of 0.5 mg/kg of apomorphine. It is observed that CRL 40827 does not modify the stereotypies induced by apomorphine in the rat.

INTERACTION WITH AMPHETAMINE

Amphetamine (2 mg/kg) is injected by the intraperitoneal route to batches of 6 rats, half an hour before administration of CRL 40827. It is noted that, except for the isolated reduction of the index of stereotypies, observed at the dose of 4 mg/kg, CRL 40827 does not modify stereotypies induced by amphetamine.

INTERACTION WITH RESERPINE

Four hours after the intraperitoneal injection of 2.5 mg/kg of reserpine, batches of 6 mice receive the CRL 40827. It is observed that, from the dose of 0.5 mg/kg, CRL 40827 clearly fights hypothermia induced by reserpine without modifying the ptosis.

INTERACTION WITH OXOTREMORINE

CRL 40827 is administered to batches of 6 mice half an hour before the intraperitoneal injection of 0.5 mg/kg of oxotremorine. It is observed that, from a dose of 0.5 mg/kg upwards, CRL 40827 antagonises the hypothermia-inducing action of oxotremorine; this effect is very clear at 32 mg/kg. Moreover, CRL 40827 does not modify the intensity of the tremors provoked by oxotremorine. Finally, CRL 40827 does not modify the signs of cholinergic peripheral stimulation which appear after administration of oxotremorine.

ACTION ON THE FOUR PLATE TEST, TRACTION AND ELECTRIC SHOCK

The test is made on batches of 10 mice, half an hour after the administration of CRL 40827. CRL 40827 does not cause increase in the number of incorrect moves which are punished; it does not bring about any major motor incapacity and, at a high does, opposes the convulsing effects of the electric shock.

ACTION ON THE SPONTANEOUS MOTILITY

Half an hour after having received CRL 40827, the micr (6 per dose, 12 controls) are placed in an actimeter where their motility is recorded for 30 minutes. It is observed that CRL 40827 virtually does not modify the spontaneous motor activity of the mouse.

ACTION WITH RESPECT TO SOME BEHAVIOUR DISTURBED BY VARIOUS AGENTS

(a) MOTILITY REDUCED BY HABITUATION TO THE CAGE

After remaining 18 hours in the actimeters, the mice (6 per dose, 12 controls) receive CRL 40827. They are immediately replaced in their respective cages and, half an hour later, their motility is recorded for 30 minutes. At a high dose (34 Mg/kg), CRL 40827 seems to provide a moderate renewal of motor activity.

(b) MOTILITY REDUCED BY HYPOXIC AGGRESSION

Half an hour after having received the CRL 40827, the mice (10 per dose, 20 controls) are subjected to acute anoxia by pressure reduction [depression of 600 mm Hg (i.e. $8 \times 10^4$ pascals) in 90 seconds, return to normal pressure in 45 seconds], then they are placed in an actimeter where their motility is recorded for 10 minutes. It is noted that CRL 40827 does not produce any improvement in the motor recovery of mice whose motility has been reduced due to a brief stay in a cage under reduced pressure.

(c) ASPHYXIC ANOXIA

Batches of 10 mice receive CRL 40827 half an hour before the intraperitoneal administration of 34 mg/kg of Gallamine Triiodoethylate. At the highest dose (34 mg/kg CRL 40827 prevents the appearance of convulsions and death in 40% of the animals.

CONCLUSION RELATIVE TO THE ACTION ON THE CNS

The antagonism of the hypothermiae induced by apomorphine, reserpine or oxotremorine makes it possible to foresee an activity of antidepressant type for the CRL 40827. These antagonisms being observed in the absence of anticholinergic effect, the CRL 40827 therefore differs from the imipraminic antidepressants.

On the other hand, the absence of antagonism of the ptosis induced by reserpine, and of motor stimulation with stereotypies makes it possible to distinguish the CRL 40827 from the IMAO and amphetaminic compounds respectively. In brief, there is a strong presumption that the CRL 40827 behaves like the adrenergic stimulants.

Furthermore, CRL 40827 exerts solely anticonvulsive effects at a high dose. Finally, it reduces the intergroup aggressiveness in the mouse.

3. Action on the cardiovascular and respiratory system

It is observed that CRL 40827 acts as hypotensive and tachycardiainducing agents in the anaesthetized dog and in the genetically hypotensive, awake rat, that it reduces the vascular resistances of the territories explored (vertebral, femoral and renal) and the total peripheral resistance, that it reduces the work of the left-hand ventricule and shortens the diastole, that it stimulates respiration, that it reduces the hypertensive effects of the noradrenaline from the dose of 1 mg/kg in the dog (the maximum effect being attained at the dose of about 10 mg/kg).

The local rates of flow of blood do not increase, but the resistances diminish; this phenomenon would imply that the CRL 40827 induces an arterial peripheral vasodilation at the same time as an increase in the veinous drainage since the cardiac output remains equal.

4. Action on the biliary secretion

In the dog anaesthetized with Nembutal, the normal biliary output collected in 30 minutes is 1.5 ml; the biliary output increases after intraduodenal injection of CRL 40827 and passes to 1.75 ml for 2.5 mg/kg of CRL 40827, to 2.25 ml for 5 mg/kg and to 2.5 ml for 10 mg/kg. In the rat anaesthetized with Nembutal, the biliary output increases 1 to 3 hours after I.V. injection of CRL 40827 at the doses of 5 mg/kg and 25 mg/kg.

5. Local anaesthetic effect

The anaesthetic effect was studied in the guinea pig after injection of CRL 40827 by the intradermic route in a volume of 0.2 ml at concentrations of 0.1, 0.5 and 1% (3 guinea pigs per dose). Each animal receives physiologcal serum, procaine and CRL 40827 in defined zones.

The test, which consists in a series of 6 injections in the injected zone is carried out 5, 10, 15, 20, 25 and 30 minutes after the injection. It is ascertained that the CRL 40827 has a local anesthetic effect when it is administered at concentrations of 0.5 and 1%.

C. Tests relative to CRL 40854 (Example 5)

CRL 40854, in solution in distilled water, was administered by the intraperitoneal route in a volume of 20 ml/kg in the male mouse and 5 ml/kg in the male rat.

1. Toxicity

The maximum non-lethal dose, LD-O, is greater than 128 mg/kg and less than 256 mg/kg in the mouse.

2. Action on the CNS

By proceeding according to the modi operandi given hereinabove, for the CRL 40827, the following is observed.

Interaction with Apomorphine

At the doses of 16 and 64 mg/kg in the mouse, CRL 40854 moderately opposes the hypothermia-inducing action of apomorphine without modifying the behaviour of verticalisation and stereotypies.

In the rat, the CRL 40854 does not modify the stereotypies induced by apomorphine.

INTERACTION WITH AMPHETAMINE

At the doses of 8 and 32 mg/kg, CRL 40854 potentialises the duration of the stereotypies induced by amphetamine.

INTERACTION WITH RESERPINE

At the doses of 4, 16 and 64 mg/kg, CRL 40854 moderately antagonises the hypothermia induced by reserpine without modifying the ptosis.

INTERACTION WITH OXOTREMORINE

At the doses of 16 and 64 mg/kg, CRL 40854 aggravates the hypothermia-inducing effect of oxotremorine. It does not modify the tremours and signs of cholinergic peripheral stimulation.

ACTION ON THE FOUR PLATE TEST, TRACTION AND ELECTRIC SHOCK

Like the CRL 40827, the CRL 40854 does not produce any increase in the number of incorrect moves which are punished and does not bring about any major motor incapacity. On the other hand, it does not modify the convulsing effects of tne electric shock.

ACTION ON THE SPONTANEOUS MOTILITY

At a high does (64 mg/kg), the CRL 40854 moderately reduces the spontaneous motility of the mouse.

ACTION WITH RESPECT TO A FEW BAHAVIOUR DISTURBED BY VARIOUS AGENTS

(a) MOTILITY REDUCED BY HABITUATION TO THE CAGE

The CRL 40854 does not provoke a clear renewal of the motor activity in the mouse habituated to its cage.

(b) MOTILITY REDUCED BY HYPOXIC AGGRESSION

Like the CRL 40827, the CRL 40854 does not produce any improvement in the motor recovery in the mouse.

(c) ASPHYXIC ANOXIA

The CRL 40854 does not modify the appearance of convulsions and death consecutive to an anoxia provoked by blocking (curarisation).

In conclusion, the CRL 40854, which reduces the intergroup aggressiveness in the mouse, has surprising results with respect to the conventional sedative and antidepressant agents.

In clinic, good results have also been obtained with CRL 40727, CRL 40827 and CRL 40827A, in the psychotropic domain as sedative and antidepressant agents in man after having been administered in the form of tablets or gelatin-coated capsules each containing 5 mg of active ingredient, at the rate of 3 tablets or gelules per day.

What is claimed is:
1. 1-(2-fluorophenyl)-2-tertiarylbutylamine-1-ethanol and its addition salts.
2. A therapeutical composition comprising 1-(2-fluorophenyl)-2-tertiarybutylamino-1-ethanol or its addition salt and at least one suitable physiological excipient.
3. An orally administered CNS-antidepressant therapeutical composition comprising the compound of claim 1 and at least one suitable physiological excipient.

* * * * *